United States Patent
Ritter

(10) Patent No.: US 10,625,012 B2
(45) Date of Patent: Apr. 21, 2020

(54) AIR SEPARATOR INCLUDING FORCED CIRCULATION

(71) Applicant: B. BRAUN AVITUM AG, Melsungen (DE)

(72) Inventor: Kai-Uwe Ritter, Melsungen (DE)

(73) Assignee: B. Braun Avitum AG (DE)

( * ) Notice: Subject to any disclaimer, the term of this patent is extended or adjusted under 35 U.S.C. 154(b) by 204 days.

(21) Appl. No.: 15/874,089

(22) Filed: Jan. 18, 2018

(65) Prior Publication Data

US 2018/0221559 A1    Aug. 9, 2018

(30) Foreign Application Priority Data

Feb. 3, 2017    (DE) .......................... 10 2017 102 175

(51) Int. Cl.
| | | |
|---|---|---|
| *B01D 53/02* | (2006.01) | |
| *A61M 1/36* | (2006.01) | |
| *B01D 19/00* | (2006.01) | |

(52) U.S. Cl.
CPC ........ *A61M 1/3638* (2014.02); *A61M 1/3627* (2013.01); *A61M 2206/14* (2013.01); *A61M 2206/16* (2013.01); *A61M 2206/20* (2013.01); *B01D 19/0057* (2013.01)

(58) Field of Classification Search
CPC .............. A61M 1/3627; A61M 1/3638; A61N 2206/14; A61N 2206/16; A61N 2206/20; B01D 19/0057

See application file for complete search history.

(56) References Cited

U.S. PATENT DOCUMENTS

| | | | |
|---|---|---|---|
| 5,632,894 A | | 5/1997 | White et al. |
| 5,849,065 A | | 12/1998 | Wojke |
| 2009/0084721 A1 | * | 4/2009 | Yardimci ............ A61M 1/1658 210/188 |
| 2011/0092875 A1 | | 4/2011 | Beck |
| 2012/0152787 A1 | | 6/2012 | Reiter et al. |
| 2014/0326646 A1 | * | 11/2014 | Strohhoefer .......... B01D 61/32 210/85 |
| 2016/0243296 A1 | * | 8/2016 | Schaefer ............ A61M 1/1043 |

FOREIGN PATENT DOCUMENTS

| | | |
|---|---|---|
| CA | 2759590 A1 | 10/2010 |
| DE | 19617036 A1 | 11/1997 |
| DE | 102009024465 B4 | 3/2015 |
| EP | 0803273 A1 | 10/1997 |
| EP | 2468321 A1 | 6/2012 |

OTHER PUBLICATIONS

Extended European Search Report for European Application No. 18 151 123.9, dated Jun. 18, 2018, with English translation, 10 pages.
German Search Report for German Application No. 10 2017 102 175.2, with translation, dated Jul. 26, 2017, 13 Pages.

* cited by examiner

*Primary Examiner* — Christopher P Jones
(74) *Attorney, Agent, or Firm* — RatnerPrestia

(57) ABSTRACT

An air separator of an extracorporeal blood treatment machine is disclosed in which a flow conducting element is arranged directly downstream of a fluid inlet of an air separator opening into an air separating chamber, the fluid inlet forcing the inflowing fluid into a flow direction at least along/tangential to the chamber periphery.

17 Claims, 4 Drawing Sheets

AIR SEPARATOR INCLUDING FORCED CIRCULATION

CROSS REFERENCE TO RELATED APPLICATIONS

This application claims priority to German application DE 10 2017 102 175.2 filed Feb. 3, 2017, the contents of such application being incorporated by reference herein.

FIELD OF THE INVENTION

The present invention relates to an air separator of a fluid-handling machine, preferably an extracorporeal blood treatment machine such as a dialysis machine, comprising a flow conducting element arranged directly downstream of a fluid inlet of an air separating chamber for generating/backing a circulating movement (turbulence) of the fluid flowing into the air separating chamber.

BACKGROUND OF THE INVENTION

Fluid-handling machines frequently require the arrangement of air separators so as to ensure the functioning of the machine itself and/or of a consumer/receiver of the fluid being located downstream thereof. In particular, in medical machines such as extracorporeal blood treatment machines or heart-lung machines that are provided for removing and re-feeding blood as the fluid to be handled from/to a (human) body, it is important to reduce so-called micro-bubbles inside the blood as a side-effect of extracorporeal blood treatment, before the blood is returned into the body.

Thus, at present it is being discussed whether said micro-bubbles have to be classified as being harmful whatsoever. In the current edition of the Standard 60601-2-16, therefore for the first time an upper limit is indicated for micro-bubbles within the blood for reasons of safety.

The development of medical machines handling fluid (blood) consequently has reacted thereto and inter alia methods of detecting micro-bubbles within a bubble size range of from 10-500 μm have been developed on the basis of a pulsed ultrasound Doppler system, for example. As a result, it was found that fluid (blood) removed from and returned to a body is enriched, due to the extracorporeal treatment, with air bubbles which consequently are likewise guided into the patient's body without any alarm being triggered. Micro-bubbles of this type probably might be the cause of minimal embolisms that may strongly damage internal organs.

Therefore, it is a basic attempt in developing fluid-handling medical machines such as extracorporeal blood treatment machines to reduce the number of micro-bubbles returned into a patient's body in order to minimize the risk for the patient.

DESCRIPTION OF THE RELATED ART

Air separators that are capable of separating (micro) air bubbles from a fluid and that are suited also for medical use in the case of fluid-handling machines such as extracorporeal blood treatment machines (dialysis machines) are known from the state of the art.

Such an air separator usually includes an upright air separating chamber funnel-shaped or cup-shaped at least in portions which comprises an upper fluid inlet (blood inlet) and a lower fluid outlet (blood outlet), with an upper air outlet being further provided. Especially, the fluid inlet is configured and orientated so that fluid flowing out of the same is made to circulate along the housing periphery in a movement superposing a generally axial flow direction, thus exerting a centrifugal force on the fluid. Said centrifugal force causes the fluid to be forced radially outwardly inside the air separating chamber, whereas air bubbles contained therein are retained primarily in the center (close to the longitudinal housing axis) and may raise within the housing toward the air outlet.

In order to obtain said circulation of the inflowing fluid, the fluid inlet is aligned along/tangentially to the housing periphery up to 90° relative to the longitudinal housing axis, thus allowing the inflow of the fluid to be deflected at most 90° relative to the longitudinal housing axis and to exit the fluid inlet horizontally at best.

This technology properly separates air bubbles mainly in the case of low flows. In the case of higher flows, the dwell time of the fluid inside the air separating chamber frequently does no longer suffice to grant enough time for the air bubbles to rise toward the air outlet. Although the effect of the fluid circulation (swirl) is still given and backs the separation of the micro air bubbles, it is considerably limited especially in the case of higher flows, however.

SUMMARY OF THE INVENTION

In view of these problems, it is an object of the present invention to provide an air separator of the afore-described species the air separating effect of which is improved especially in the case of higher flows as compared to the known state of the art.

This object is achieved by an air separator comprising the features of the independent claim. Advantageous configurations of the invention are the subject matter of the dependent claims.

Consequently, it is the core of the present invention to arrange a flow conducting element (directly) downstream of the fluid inlet of an air separator leading toward an air separating chamber, by which flow conducting element the inflowing fluid is forced into a flow direction at least along/tangentially to the chamber periphery. The fluid can be guided by the flow conducting element via a flow path longer than those known from prior art along a predefined spiral path so as to obtain higher centrifugal forces as well as longer dwell times of the fluid within the air separating chamber. This results in a separation improved with respect to the known state of the art of (micro) air bubbles in the blood, for example, —even in the case of higher flows. Moreover, it has turned out that, in the case of improper operation, such flow conducting element has an advantageous influence on the function of the air separator. Should the fill level of the air separating chamber drop to an (undesired) low value, the fluid (blood) flowing out of the fluid outlet does no longer simply drip onto the surface of the fluid still present in the chamber, but is guided further downwards as well as along the chamber wall so that then it is running downwards on the chamber wall. In this way, the generation of air bubbles and the formation of foam undesired in this case which is due to fluid drops impinging on the fluid surface in an uncontrolled manner are avoided or, respectively, reduced.

According to a preferred aspect of the present invention, which may have to be independently claimed, it is provided that the flow conducting element at least in portions takes the cross-sectional shape of a groove. This helps achieve better forced guiding of the inflowing fluid.

According to a further preferred aspect of the present invention, which may have to be independently claimed, it is further provided that the groove in its upper segment extends substantially axially in parallel to the fluid inlet and preferably axially in parallel to the chamber axis and, further preferred, is adjacent to the fluid inlet substantially by form closure. In this way, turbulences in the area between the fluid inlet and the flow conducting element can be avoided/reduced so as to prevent formation of foam of the inflowing fluid.

According to a further preferred aspect of the present invention, which may have to be independently claimed, it is further provided that the groove extends in spiral shape along the peripheral wall of the air separating chamber toward the lower fluid outlet and at its runout is orientated at least perpendicularly to the chamber axis, preferably upwards at an angle. This helps accelerate the fluid forcedly guided by the flow conducting element inside the air separating chamber even upwardly again and thus extend the dwell time thereof inside the chamber.

According to a further preferred aspect of the present invention, which may have to be independently claimed, it is further provided that the groove is orientated upwardly at its runout at an angle of about 30° with the longitudinal chamber axis. Said angle has stood the test in so far as, in this way, sufficient acceleration of the fluid toward the top can be achieved and simultaneously undesired turbulences especially in the case of blood as the inflowing fluid are avoided.

According to a further preferred aspect of the present invention, which may have to be independently claimed, it is moreover provided that the flow conducting element is inserted as a separate component in the air separating chamber or is attached to the air separating chamber or is integrated in the wall of the air separating chamber (on the inside or the outside).

In accordance with a further preferred aspect of the invention, which may have to be independently claimed, it is moreover provided that the flow conducting element follows the chamber periphery at least by about 30°, preferably by 90°-180° and at most by 360°.

In accordance with a further preferred aspect of the invention, which may have to be independently claimed, the air separator includes a deflector wall extending in the peripheral chamber direction which is arranged on the side of the fluid inlet facing away from the flow conducting element and creates a smooth transition, when viewed in the peripheral direction, between the chamber wall and the fluid inlet in the form of a nozzle protruding in the axial chamber direction. In other words, the fluid inlet protrudes into the air separating chamber preferably in a nozzle/tubular shape as well as axially in parallel, wherein an upper segment of the groove is preferably directly connected initially likewise axially in parallel to the fluid inlet so as to then smoothly merge into a spiral shape in the type of a water slide. Thus, the outflowing and forcedly guided fluid may flow quasi behind the inlet nozzle, when viewed in the peripheral direction, with said inlet nozzle then acting as an obstacle to flow. To avoid this, the deflector wall is provided which causes a smooth transition of the inner chamber wall to the inlet nozzle and thus guides the upwardly accelerated and then circulating fluid past the inlet nozzle.

According to a further preferred aspect of the invention, which may have to be independently claimed, it is moreover provided that the groove width at least in its upper segment substantially corresponds to the diameter of the fluid inlet and widens or narrows preferably toward its lower segment. This helps realize different flow rates with different centrifugal forces and adjust the same as a function of the chamber size and the chamber shape.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 4:
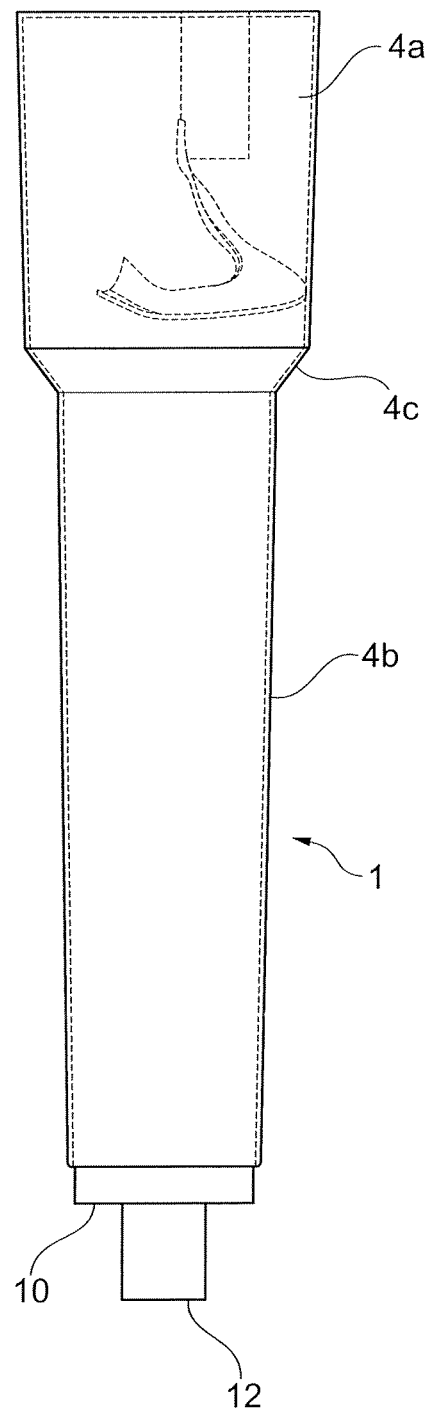
FIG. 4 shows the partially transparent side view of the entire air separator according to aspects of the present invention.

The air separator 1 according to a preferred embodiment of the present invention shown in FIG. 4 in a side view is configured to be preferably inserted into the extracorporeal blood circulation of an extracorporeal blood treatment machine such as a dialysis machine of a generally known structure. In the air separator according to aspects of the invention, a flow conducting element 2 is arranged directly downstream of a fluid inlet 6 of the air separator 1 opening into a (cylindrical/cup-shaped) air separating chamber 4 with which fluid inlet an inflowing fluid, preferably blood, is forced in a direction of flow at least along/tangentially to the chamber periphery.

The usually vertically orientated air separating chamber 4 in the present case includes two substantially cylindrical or cup-shaped axial portions 4a, 4b of different diameter, wherein the upper axial portion having a large diameter 4a being joined to the lower axial portion having a small diameter 4b via a funnel-shaped constriction 4c.

The upper axial portion 4a is closed on the front end with a chamber lid 8 in which each of the fluid inlet 6 preferably in the form of an (inlet) nozzle protruding into the upper axial portion 4a of the air separating chamber 4 vertically/in parallel to the chamber axis and an air outlet not shown in detail are formed/arranged to be out of center. The lower axial portion 4b is closed at the front end with a chamber bottom 10 in which a fluid outlet 12 is arranged centrally or out of center.

This structure and the dimensioning of the air separating chamber 4 including the upper and lower axial chamber portions 4a, 4b thereof, especially in the area of the extracorporeal blood treatment machine, correspond to the structure well-known from the state of the art so that a more detailed indication of the individual dimensions is unnecessary in this context.

Figure 1:
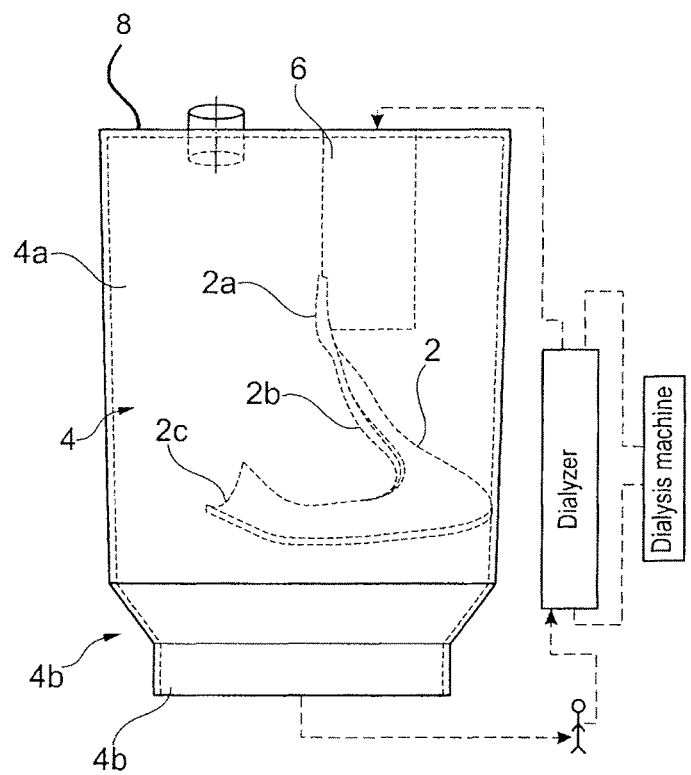
FIG. 1 shows the partially transparent side view of an upper portion of an air separating chamber according to aspects of the present invention.
Figure 2:
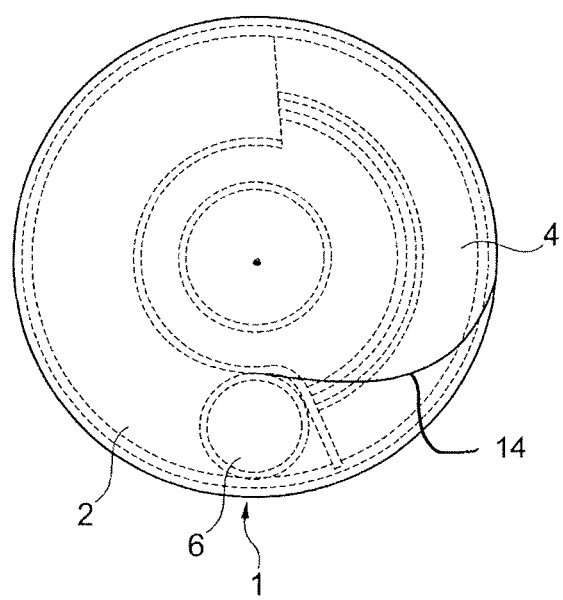
FIG. 2 shows the partially transparent top view of the air separating chamber of the air separator according to FIG. 1.
Figure 3:
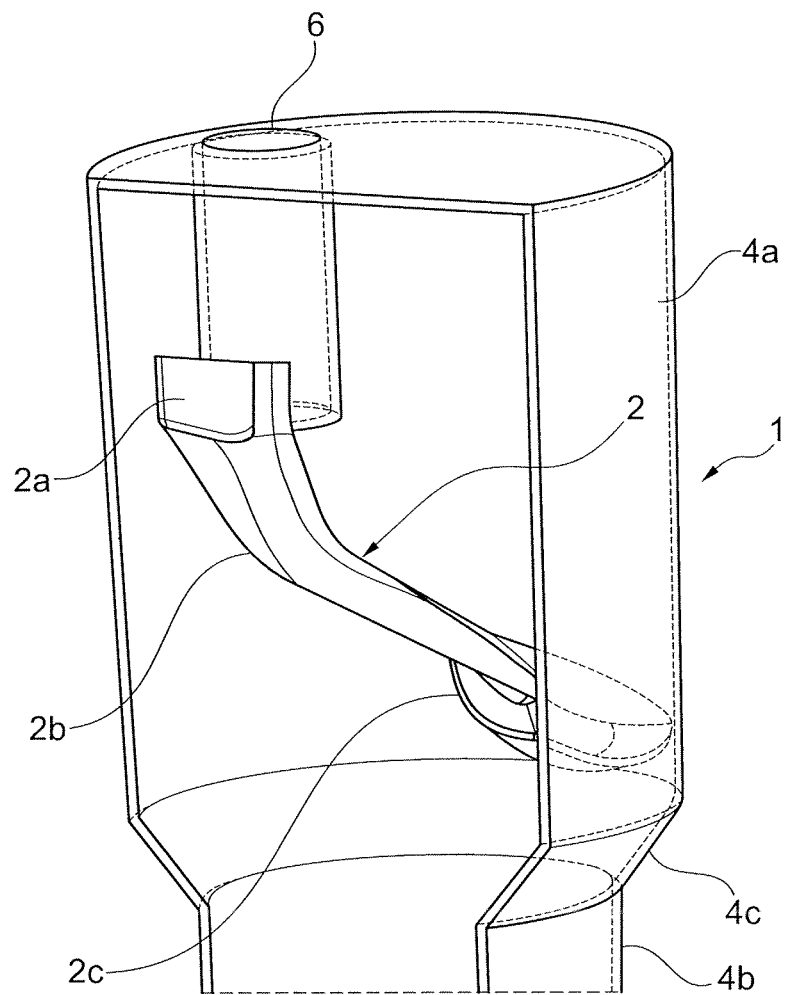
FIG. 3 shows the partially transparent side view of the upper portion of the air separating chamber according to FIG. 1, but in a viewing direction rotated about approx. 90°.

The flow conducting element 2 arranged downstream of the fluid inlet 6 in the present preferred embodiment according to FIGS. 1 to 3 includes a slide extending spirally along the chamber wall of the upper axial portion 4a and taking a U or groove shape in cross-section which at its upper/ uppermost segment 2a extends (substantially) vertically/in parallel to the chamber axis, in a central segment 2b smoothly merges into a (substantially) horizontal contour (aligned perpendicularly to the chamber axis) and finally at its lower/lowermost segment 2c ends in a type of jump which is orientated (substantially) horizontally and preferably slightly upwards.

In order to avoid turbulences in the transition between the inlet nozzle 6 and the slide 2 the upper segment 2a of the latter is adjacent to the inlet nozzle 6 (preferably) by form closure so as to avoid dead spaces.

As already indicated in the foregoing, the slide 2 may preferably be upwardly directed in the runout (jump) 2c, Preferably, the jump 2c is pulled upwards by about 30° relative to the horizontal.

Depending on the configuration, the slide 2 may be a separate/additional element incorporated/connected in/to the air separating chamber 4 which may be joined to or dismounted from the air separating chamber 4, as required. Alternatively, it is also possible to integrate the slide 2 in the chamber wall so that the air separating chamber 4 and the slide 2 can be made from one single part.

Basically, the slide 2 takes a spiral shape including an angle of rotation of about 30°, preferably 90 to 180° and maximally 360°. The axial extension is individually adapted to the axial length of the upper axial chamber portion 4a and ends directly ahead of the funnel-shaped transition 4c to the lower axial chamber portion 4b.

Since the jump 2c of the slide 2 is directed preferably upwardly, the inflowing blood is accelerated upwardly so that the upwardly accelerated blood may flow transversely, where appropriate, around the inlet nozzle 6 usually arranged out of center. In this case, the inlet nozzle 6 would constitute a flow obstacle of the upwardly accelerated blood circulating along the chamber wall. In order to avoid this, a deflector wall 14 is provided which provides a smooth transition between the chamber wall and the inlet nozzle 6 on the nozzle side facing away from the slide 2 and which guides the blood specifically past the inlet nozzle 6.

The cross-section of the slide 2 is preferably adapted to the diameter of the inlet nozzle 6 and (substantially) corresponds to the same. Further preferred, the slide cross-section remains constant over the entire length thereof, but may widen or narrow toward the jump 2c.

During operation, the air separating chamber 4 is preferably completely filled with blood, i.e. almost up to the upper chamber lid 8. Should the chamber 4 erroneously be filled only partially with blood, care has to be taken that the blood level is/remains at least so high that the slide 2 and the inner opening of the inlet nozzle 6 are located below the blood surface. In this state, a major part of the inflowing fluid (blood) is first accelerated upwards, as desired, and in so doing is made to circulate so that it spins around at least one to several times, thus enabling air bubbles to be separated.

The flow in the lower axial portion of the air separating chamber 4 is comparatively unhindered, without any turbulences and (substantially) without any rotation. This means also that the lower axial portion 4b of the air separator 1 may be shortened as compared to the known state of the art, whereas the volume of the upper axial portion 4a may be increased as compared to the known state of the art.

Figure 5A:
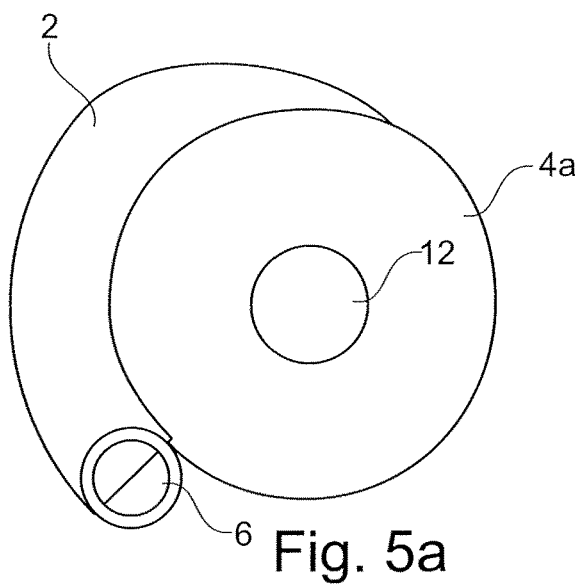
FIGS. 5a, 5b, and 5c show the schematic top views of three further modifications of an air separator according to aspects of the present invention.
Figure 5B:
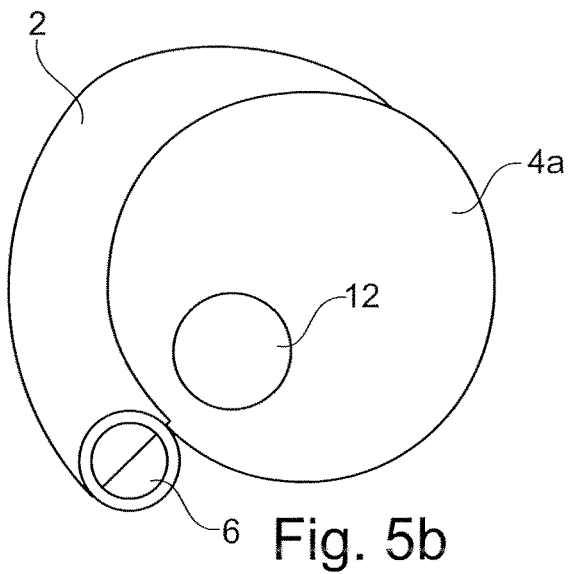
Figure 5C:
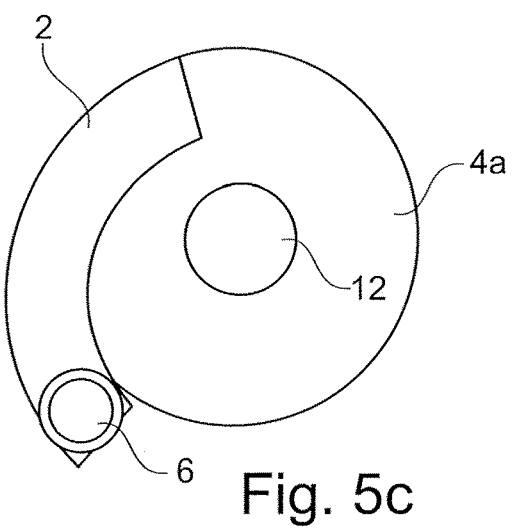

In FIGS. 5a-5c, alternative configurations of the afore-described preferred embodiment are illustrated which follow the same operating principle as the afore-described embodiment, however.

Accordingly, in the air separating chamber 4 according to FIG. 5a the fluid inlet nozzle 6 is arranged outside the circular/cylindrical contour of the upper axial portion 4a of the air separating chamber 4. The slide 2 arranged directly downstream of the nozzle 6 follows the upper axial portion 4a on the outside by about 30°, preferably 90-180°, maximally 360°, which is comparable to the afore-described embodiment. The slide cross-section may remain constant, widen or narrow along the slide contour. In the lower slide segment (zone of the jump) 2c the slide 2 merges into the circular air separating chamber 4 in the upper axial portion 4a thereof. This configuration possibly improves the circulation inside the circular area of the air separating chamber 2 shown in FIG. 5a as compared to the afore-described embodiment, because the inlet nozzle 6 does no longer constitute any flow obstacle.

The variant according to FIG. 5b differs from the variant according to FIG. 5a by the positioning of the fluid outlet 12 in the lower axial portion 4b of the air separating chamber 4. Accordingly, the fluid outlet 12 is placed centrally (on the chamber axis) in the variant according to FIG. 5a, whereas the fluid outlet in the variant according to FIG. 5b is offset out of center (in the direction of the chamber wall), preferably in the direction of the peripheral positioning of the fluid inlet 6.

Finally, FIG. 5c shows a third variant of the air separator 1 according to aspects of the invention, according to which the fluid inlet nozzle 6 is also disposed outside the air separating chamber 4 circular in cross-section and the slide 2 follows the contour of the upper axial portion 4a of the chamber 4 at first on the outside, but then rotates into the upper axial portion 4a in the full width.

As is illustrated in FIG. 5c, the slide 2 then follows the chamber contour over a particular angular distance at the inner chamber wall side thereof so as to finally end in the jump 2c described in the beginning. In this variant, too, the slide 2 may remain constant, widen or narrow in its cross-section.

The invention claimed is:

1. An air separator of a fluid-handling machine comprising:
    an air separating chamber having a longitudinal chamber axis and including an upper fluid inlet and a lower fluid outlet;
    a flow conducting element arranged directly downstream of the upper fluid inlet of the air separating chamber for generating or increasing a circulating movement of the fluid flowing into the air separating chamber and flowing toward the lower fluid outlet of the air separating chamber, wherein at least a portion of the flow conducting element has a cross-sectional shape of a groove extending downwardly from an upper segment along the longitudinal chamber axis in spiral shape along a peripheral wall of the air separating chamber toward the lower fluid outlet, and ending at a runout that is oriented upwardly at an angle relative to the longitudinal chamber axis.

2. The air separator according to claim 1, wherein the upper segment extends parallel to the fluid inlet.

3. The air separator according to claim 2, wherein the upper segment extends parallel to the longitudinal chamber axis, the longitudinal chamber axis comprising a central cylindrical axis of the air separating chamber.

4. The air separator according to claim 3, wherein the upper segment is adjacent to the fluid inlet.

5. The air separator according to claim 1, wherein the groove at the runout is oriented upwardly at an angle of about 30° relative to the longitudinal chamber axis.

6. The air separator according to claim 1, wherein the flow conducting element and the air separating chamber are separate components.

7. The air separator according to claim 1, wherein the flow conducting element is integrated in a wall of the air separating chamber.

8. The air separator according to claim 1, wherein the flow conducting element follows the peripheral wall of the chamber in spiral shape at least by about 30°.

9. The air separator according to claim 8, wherein the flow conducting element follows the peripheral wall of the chamber in spiral shape by about 90° to about 180°.

10. The air separator according to claim 8, wherein the flow conducting element follows the peripheral wall of the chamber in spiral shape by a maximum of 360°.

11. The air separator according to claim 1, further comprising:
    a deflector wall extending in a direction of a periphery of the chamber, the deflector wall arranged on a side of the fluid inlet facing away from the flow conducting element and, when viewed from the periphery of the chamber, creates a smooth transition between a wall of the chamber and the fluid inlet.

12. The air separator according to claim 11, wherein the smooth transition forms a nozzle protruding in an axial direction of the chamber.

13. The air separator according to claim 1, wherein a width of the groove substantially corresponds, at least in an upper segment of the groove, to a diameter of the fluid inlet and widens or narrows in the direction of a lower segment of the groove.

14. The air separator according to claim 1, wherein the fluid-handling machine is an extracorporeal blood treatment machine.

15. The air separator according to claim 14, wherein the extracorporeal blood treatment machine is a dialysis machine.

16. An air separator of a fluid-handling machine comprising:
    an air separating chamber having a longitudinal chamber axis comprising a central cylindrical axis of the air separating chamber, and including an upper fluid inlet and a lower fluid outlet;
    a flow conducting element arranged directly downstream of the upper fluid inlet of the air separating chamber for generating or increasing a circulating movement of the fluid flowing into the air separating chamber and flowing toward the lower fluid outlet of the air separating chamber, wherein at least a portion of the flow conducting element has a cross-sectional shape of a groove including a runout oriented perpendicularly to the longitudinal chamber axis;
    wherein the upper segment extends parallel to the fluid inlet and the longitudinal chamber axis.

17. An air separator of a fluid-handling machine comprising:
    an air separating chamber having a longitudinal chamber axis and including an upper fluid inlet and a lower fluid outlet;
    a flow conducting element arranged directly downstream of the upper fluid inlet of the air separating chamber for generating or increasing a circulating movement of the fluid flowing into the air separating chamber and flowing toward the lower fluid outlet of the air separating chamber, wherein at least a portion of the flow conducting element has a cross-sectional shape of a groove including a runout oriented perpendicularly to the longitudinal chamber axis; and
    a deflector wall extending in a direction of a periphery of the chamber, the deflector wall arranged on a side of the fluid inlet facing away from the flow conducting element and, when viewed from the periphery of the chamber, creates a smooth transition between a wall of the chamber and the fluid inlet;
    wherein the smooth transition forms a nozzle protruding in an axial direction of the chamber.

* * * * *